(12) United States Patent
Sugita

(10) Patent No.: US 8,274,660 B2
(45) Date of Patent: Sep. 25, 2012

(54) OPTICAL TOMOGRAPHIC IMAGING APPARATUS

(75) Inventor: Mitsuro Sugita, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 219 days.

(21) Appl. No.: 12/683,461

(22) Filed: Jan. 7, 2010

(65) Prior Publication Data

US 2010/0181462 A1 Jul. 22, 2010

(30) Foreign Application Priority Data

Jan. 22, 2009 (JP) ................................ 2009-011619

(51) Int. Cl.
*G01B 9/02* (2006.01)

(52) U.S. Cl. ..................................................... 356/479

(58) Field of Classification Search .................. 356/479, 356/497
See application file for complete search history.

(56) References Cited

U.S. PATENT DOCUMENTS

| 6,293,674 | B1 | 9/2001 | Huang et al. | |
|---|---|---|---|---|
| 7,557,931 | B2 * | 7/2009 | Toida | 356/497 |
| 2006/0221350 | A1 | 10/2006 | Murphy et al. | |
| 2010/0166293 | A1 * | 7/2010 | Sugita et al. | 382/154 |

FOREIGN PATENT DOCUMENTS

| EP | 1775545 A2 | 4/2007 |
|---|---|---|
| JP | 2007-054251 | 3/2007 |
| JP | 2007-101250 | 4/2007 |
| WO | 2008/139799 A1 | 11/2008 |

OTHER PUBLICATIONS

Communication dated Mar. 21, 2011, forwarding a European Search Report dated Mar. 11, 2011, in counterpart European Application No. 10151279.6-2213/2211140.
Notification of the First Office Action dated Jun. 22, 2011, in counterpart Chinese Application No. 201010005421.5.
U.S. Appl. No. 12/296,400, filed Oct. 7, 2008.

* cited by examiner

Primary Examiner — Tarifur Chowdhury
Assistant Examiner — Jonathon Cook
(74) Attorney, Agent, or Firm — Fitzpatrick, Cella, Harper & Scinto

(57) ABSTRACT

Provided is an optical tomographic imaging apparatus that is capable of shortening a period of time of focusing at multiple focus positions when images split in a depth direction are obtained by zone focusing. The optical tomographic imaging apparatus includes: a focus position setting device for splitting a zone within a predetermined imaging depth range into multiple focus zones so as to set multiple focus positions; a reference position setting device for setting at least two reference positions in an imaging depth direction within the predetermined imaging depth range; and a focus controlling device for performing focusing at the multiple focus positions sequentially based on focus position information generated by the focus position setting device and a focus condition of an in-focus state for the at least two reference positions set in advance by the reference position setting device.

7 Claims, 11 Drawing Sheets

OPTICAL TOMOGRAPHIC IMAGING APPARATUS

BACKGROUND OF THE INVENTION

1. Field of the Invention

The present invention relates to an optical tomographic imaging apparatus, and more particularly, to an optical tomographic imaging apparatus that is used for opthalmological care, tomographic observation of skin, tomography scan of a digestive and cardiovascular wall with an endoscope or a catheter constituted of the optical tomographic imaging apparatus, or the like.

2. Description of the Related Art

In recent years, an optical interference tomographic imaging method and an optical interference tomographic imaging apparatus, to which a low coherence interferometer technology or a white light interferometer technology is applied, are in actual use.

In particular, an optical tomographic imaging apparatus (optical interference tomographic imaging apparatus) that performs an optical coherence tomography (OCT) utilizing interference phenomenon of multi-wavelength light may be used to obtain a tomographic image of a sample with high resolution.

Therefore, in the opthalmological field, an optical tomographic imaging apparatus is becoming an indispensable apparatus for obtaining a tomographic image of a fundus or a retina.

In addition to the opthalmological application, the optical tomographic imaging apparatus has also been used for tomographic observation of skin, tomography scan of a digestive and cardiovascular wall with an endoscope or a catheter constituted of the apparatus, or the like. Hereinafter, the optical tomographic imaging apparatus is referred to as an OCT apparatus.

When imaging a living organism, a disturbance of the image due to a motion of the living organism (so-called a motion artifact) becomes a problem with the OCT apparatus in various applications. In particular, in the OCT apparatus for the ophthalmological image diagnosis, existence of an eye movement largely affects accuracy of diagnosis.

As a typical eye movement, a motion of approximately 100 μm per second occurs both in the in-plane direction of the fundus (hereinafter referred to as a horizontal direction) and in the depth direction thereof (hereinafter referred to as a vertical direction) in a three-dimensional manner.

Therefore, by an OCT apparatus of time-domain method, which was first put into practical use in the opthalmological application, a three-dimensional image technically could not be obtained because it requires a long period of time for imaging.

In this method, the imaging time is up to approximately one second for one B scan cross section image (two-dimensional image including one-dimensional image of the horizontal direction and one-dimensional image of the vertical direction). Therefore, a relatively long period of time is necessary for obtaining approximately 100 shots of B scan cross section images that are necessary for obtaining the three-dimensional image, and hence it is not practical because the motion artifact occurring due to the eye movement during the period is large.

For this reason, high speed performance of the OCT apparatus has further been desired.

In recent years, an OCT apparatus of a Fourier domain method (hereinafter referred to as an FD-OCT apparatus) has been widespread in use for its high speed performance that is at least ten times as fast as that of the conventional time-domain method.

Next, a schematic structure of this FD-OCT apparatus is described.

FIG. 10A is a schematic diagram of a typical FD-OCT apparatus for an opthalmological use.

In FIG. 10A, a light beams emitted from a light source 1001 is guided by a single mode optical fiber 1002 and enters a fiber optical coupler 1003.

The fiber optical coupler 1003 is a so-called 2×2 type, which splits the incident light from the fiber 1002 to be caused to enter two output fibers.

One of the output fibers is coupled to an imaging optical system for human fundus that is a signalling beams path of a Michelson interferometer, and the other output fiber is coupled to a reference beams path of the interferometer.

In the signalling beams path, the light output from a fiber end is converted into a parallel beams by a collimate lens 1004, propagates in space, and enters an XY scanner 1005.

The XY scanner 1005 is a reflection type optical scanning apparatus that performs two-dimensional reflection angle control, and hence a reflected signalling beams is guided by a scanning lens 1006 and an ocular lens 1007 so as to enter a human eye 1008.

The XY scanner, the scanning lens and the ocular lens constitute a scanning optical system, which focuses the signalling beams as the parallel beams onto a fundus observation target region 1009 together with an optical action of the eye, and the focus position scans a surface of the fundus that is substantially perpendicular to the optical axis in a two-dimensional manner.

The ocular lens 1007 works to adjust the focus position in the depth direction. Control for scanning and focus is performed by a controlling and signal processing device 1101 that is connected to the XY scanner 1005 and a focus driving actuator 1010, in an integrative manner including other control.

A reflection beams from the fundus observation target region 1009 and a signalling beams propagating backward in substantially the same optical path among the backscattered light beams pass through the collimate lens 1004 again and returns to the fiber optical coupler 1003.

On the other hand, the reference beams is split by the fiber optical coupler 1003, is converted into a parallel beams by the collimate lens 1004, and is reflected by a reference beams mirror 1011 disposed on an optical delay driving apparatus 1012 so as to propagate backward along the optical path.

The position of the reference beams mirror 1011 is adjusted and controlled by controlling the optical delay driving apparatus 1012 together with, in particular, correction of an axial length that is different among individuals so that a total optical path length of the reference beams path becomes a predetermined length with the signalling beams path as a reference.

A translational stage including the reference beams mirror 1011 is connected to the controlling and signal processing device 1101 and is controlled together with other control in an integrative manner.

The reference beams propagating backward passes through the collimate lens 1004 again and returns to the fiber optical coupler 1003.

The signalling beams and the reference beams which have returned to the fiber optical coupler 1003 are split individually into components returning to the light source 1001 and components directed to an interfering beams receiving system. The signalling beams and the reference beams propagate in the same single mode fiber, i.e., are superimposed with each other so as to cause optical interference.

The interfering beams receiving system is a spectroscope in this example of the conventional technique, and the OCT apparatus constitutes a so-called spectral domain OCT apparatus (hereinafter referred to as an SD-OCT).

The interfering beams is converted into a parallel beams by the collimate lens 1004 and guided to a diffraction grating 1014 by a reflecting mirror 1013, and an action of the diffraction grating causes a first order diffraction light of the interfering beams to be directed to different angles according to a wavelength component contained in the same.

The individual wavelength components of the interfering beams that enter an imaging lens 1015 at different angles are focused for imaging at different positions on a line sensor 1016 according to the angles, and are read out as light intensities corresponding to individual pixels of the line sensor so that a signal thereof is sent to the controlling and signal processing device 1101.

Next, a structure and an action of the controlling and signal processing device 1101 are described with reference to FIG. 10B.

The controlling and signal processing device 1101 controls the XY scanner 1005, the optical delay driving apparatus 1012, the focus driving actuator 1010 and the line sensor 1016, and includes drivers and an acquisition unit for acquiring signals sent after detecting the angle, the position and the optical signal. Among the signals, a line image acquisition unit 1107 receives a light intensity signal train transmitted from the line sensor, and an FFT processing unit 1108 performs inverse fast Fourier transform on the signal train, and hence a result of the process is sent to a central processing unit 1103.

The central processing unit 1103 receives a digital optical interference signal sent after the inverse Fourier transform in time series and compares the digital optical interference signal with the following signals.

The digital optical interference signal is compared with a scanner position signal and a synchronizing signal from an XY scanner driver 1102, a delay position signal and a synchronizing signal from an optical delay driver 1105, and a focus position signal from a focus driver 1106.

Thus, the optical interference signal is associated with a position on the fundus observation target region.

After that, the optical interference signal is assigned to each of predetermined pixels, and hence the image is formed and displayed on an image displaying unit 1104.

Such an FD-OCT apparatus enables three-dimensional measurement of a fundus in an imaging time of approximately 1 to 3 seconds.

On the other hand, with regard to the OCT apparatus for opthalmological use, an OCT apparatus having higher performance is demanded for early detection of diabetic retinopathy, glaucoma and age-related macular degeneration that are three major diseases that can cause loss of sight.

Specifically, an OCT apparatus having high resolution is demanded for detecting a minute change of a lesion in early stage.

An object to be imaged and measured is, for example, a change in an optic nerve fiber, a photoreceptor cell or a microvessel.

Among the resolutions, a vertical resolution, i.e., a resolution in the depth direction depends on characteristics of the light source used for the OCT apparatus. Therefore, the OCT apparatus has been devised to enlarge a wavelength width of light from the light source.

On the other hand, a horizontal resolution has a trade-off relationship with an optical spot size and a depth of focus. Therefore, simply constituting a focusing optical system having high numerical aperture (NA) is not sufficient.

The above-mentioned point is described below concretely with reference to equations and numerical examples.

The resolution of the OCT apparatus can be discussed as two resolutions in the cross section direction (vertical direction) and in the horizontal direction that is perpendicular to the cross section.

Among the two resolutions, the resolution in the cross section direction is determined by a wavelength width of light from the light source. As the wavelength width is larger, the resolution in the cross section direction is higher.

In other words, a narrow range in the vertical direction is rendered. The vertical resolution (Rz) is inversely proportional to a wavelength width of light from the light source, or in a strict sense, a wavelength width Δλ that is detected by the system after receiving light from the light source. The vertical resolution (Rz) is expressed by (Equation 1) below.

$$Rz = kz \times (\lambda^2 / \Delta\lambda) \quad \text{(Equation 1)}$$

where kz represents a constant that is approximately 0.4.

In a practical OCT for opthalmological use, Δλ has been improved up to approximately 30 to 50 nm, and currently up to approximately 100 nm, while the corresponding vertical resolution is approximately 3 μm, which is becoming close to a modification in cell level described above.

On the other hand, the resolution (Rxy) in the horizontal direction is determined by an optical imaging resolution.

In other words, the resolution (Rxy) in the horizontal direction is determined by a numerical aperture (NA) of the imaging system and accompanying optical aberration.

Supposing that there is no aberration, the horizontal resolution is expressed by (Equation 2) below.

$$Rxy = k1 \times (\lambda / NA) \quad \text{(Equation 2)}$$

where k1 is a constant that is approximately 0.5.

On the other hand, a depth of focus (DOF) of the imaging system is expressed by (Equation 3) below.

$$DOF = k2 \times (\lambda / NA^2)$$

where k2 is a constant that is approximately 0.6.

In other words, high horizontal resolution and large depth of focus have a trade-off relationship based on an optical principle. For instance, if the horizontal resolution is doubled and the diameter of the optical spot size is halved, the depth of focus becomes one fourth as being inversely proportional to the square.

In a fundus diagnosis apparatus in which the OCT is most practical, numerical values of λ=0.84 μm and NA=0.02 approximately are used, for example. If these numerical examples and the above-mentioned (Equation 2) and (Equation 3) are used, there are derived Rxy=20 μm and DOF=2 mm approximately.

The thickness of a retina of a human eye is approximately 0.5 to 1 mm. For easiness of measurement and for avoiding a deviation from the imaging range due to various movements, an imaging range of approximately 2 mm in the depth direction is usually secured.

This is derived as a DOF value, and therefore the horizontal resolution is controlled to be 20 μm at most as the diameter of the optical spot size. This value of resolution is low by approximately one digit compared with 3 μm of the vertical resolution, but it is difficult to obtain a higher horizontal resolution with a simple structure.

In contrast, Japanese Patent Application Laid-Open No. 2007-101250 discloses a zone focusing OCT apparatus, in which multiple focus zones of high NA optical system having a small DOF are set, and images split in the depth direction are recombined, to thereby obtain high horizontal resolution over a wide range of depth of focus.

Such a zone focusing can be achieved by driving the focusing lens to be at multiple focus positions, focusing in a sequential manner while performing the imaging process, and recombining the images split in the depth direction.

In addition, Japanese Patent Application Laid-Open No. 2007-54251 discloses a method of calculating and setting a drive position of the focusing lens based on a specific position as a reference.

SUMMARY OF THE INVENTION

However, the OCT apparatus described above as a conventional example has problems as follows.

The OCT apparatus is required to perform the imaging process in a period of time as short as possible. In particular, if the structure as described above is used for an OCT apparatus for opthalmological use, it is very important to shorten the imaging time so as to reduce a load on an opthalmological patient to be tested.

However, Japanese Patent Application Laid-Open No. 2007-101250 does not disclose anything about performing the serial jobs regarding the zone focusing in the OCT apparatus efficiently in a short period of time, in which the serial jobs including driving the focusing lens to be at multiple focus positions, and focusing in a sequential manner while performing the imaging process.

In particular, if the NA is increased for obtaining high horizontal resolution in the zone focusing as described above, the depth of focus is decreased on the contrary, resulting in that the number of focus zones to be obtained by splitting in the zone focusing is increased. Therefore, an efficient focusing process therefor is necessary.

The above-mentioned points are further described. In the OCT for opthalmological use, the focusing optical system for an object such as a retina of a human eye includes a biological optical system such as a cornea, a crystalline lens, and a hyaloid body of the human eye, and it is known that the biological optical system is different depending on an object to be tested due to an individual variation.

In particular, if the NA is increased for realizing the OCT with high horizontal resolution, it is necessary to increase a beams diameter of the substantially parallel beams entering the iris.

However, if the beams diameter is increased, the individual variation of the biological optical systems of human eyes is further increased. This is because an influence of the aberration increases.

The aberration of a human eye includes so-called spherical aberration, comatic aberration, astigmatism and the like, which leads to a larger influence as the beams diameter is increased.

Even if the focusing process is to be performed so that the optical spot size on the retina is decreased, it is difficult to define the optimal focus position optically and uniquely in the case where various aberrations exist due to the individual variation.

Therefore, the focusing process is actually performed by monitoring the image itself so that the desired OCT image is improved, but this method with monitoring is not suitable for the case where the number of focus zones is large.

In other words, if the NA is increased for obtaining high horizontal resolution, the depth of focus is decreased on the contrary, and hence the number of focus zones to be obtained by splitting in the zone focusing is increased as described above.

Several examples of these values are shown in Table 1.

For imaging with high horizontal resolution, 10 to 30 zones are necessary so that the focusing process is required to be performed for this number. Therefore, it is not suitable to adopt the method of monitoring the image itself while performing the focusing process so that the image to be obtained by the OCT apparatus is improved.

In contrast, according to the OCT apparatus using the above-mentioned zone focusing, focusing may be performed in a sequential manner in many focus zones (at many focus positions) while performing the imaging process.

However, Japanese Patent Application Laid-Open No. 2007-101250 does not disclose anything about performing the serial jobs in the OCT apparatus efficiently in a period of time as short as possible, as described above.

In addition, Japanese Patent Application Laid-Open No. 2007-54251 discloses that the tomographic measuring apparatus which calculates and sets a drive position of the focusing lens based on a specific position as a reference.

However, nothing is disclosed about dealing with the difference of the biological optical system such as a human eye due to the individual variation as described above and about performing the above-mentioned zone focusing efficiently.

TABLE 1

| Number of C scans in FD-OCT | | Measurement | Number of split |
|---|---|---|---|
| horizontal resolution (μm) | Depth of focus (μm) | range in depth direction (mm) | focus zones in depth direction in FD-OCT |
| 20 | 2,000 | 2 | 1 |
| 8 | 160 | 2 | 13 |
| 5 | 63 | 1 | 16 |
| 3 | 23 | 0.5 | 23 |

The present invention has been made in view of the above-mentioned problems, and it is therefore an object of the present invention to provide an optical tomographic imaging apparatus that is capable of shortening a period of time of focusing at multiple focus positions when images split in a depth direction are obtained by zone focusing.

The present invention provides an optical tomographic imaging apparatus having the following structure.

According to one aspect of the present invention, there is provided an optical tomographic imaging apparatus for taking a tomographic image of an object by splitting a light beams from a light source into a measuring beams and a reference beams, guiding the measuring beams to the object by scanning through a scanning optical system, guiding the reference beams to a reference beams mirror, and using a return beams corresponding to the measuring beams one of reflected and scattered by the object and the reference beams reflected by the reference beams mirror, to thereby image an optical tomographic image by zone focusing in which images obtained by splitting the tomographic image in a depth direction are recombined, the optical tomographic imaging apparatus including: a focus position setting device for splitting a zone within a predetermined imaging depth range into multiple focus zones so as to set multiple focus positions; a reference position setting device for setting at least two reference positions in an imaging depth direction within the predetermined imaging depth range; and a focus controlling device for performing control so as to perform focusing at the multiple focus positions sequentially based on focus position information generated by the focus position setting device and a focus condition of in-focus at the at least two reference positions set in advance by the reference position setting device.

Further, according to another aspect of the present invention, there is provided an imaging method of taking a tomographic image of an object by splitting a light beams from a light source into a measuring beams and a reference beams, guiding the measuring beams to the object through scanning with a scanning optical system, and using a return beams corresponding to the measuring beams one of reflected and scattered by the object and the reference beams, the imaging method including: a first setting step of splitting a zone within a predetermined imaging depth range into multiple focus zones so as to set multiple focus positions; a second setting step of setting at least two reference positions in an imaging depth direction within the predetermined imaging depth range; and a control step of performing control so as to perform focusing at the multiple focus positions sequentially based on focus position information set in the first setting step and a focus condition of in-focus at the at least two reference positions set in advance in the second setting step.

According to the present invention, the optical tomographic imaging apparatus that is capable of shortening the period of time of focusing at the multiple focus positions when the images split in the depth direction are obtained by the zone focusing.

Further features of the present invention will become apparent from the following description of exemplary embodiments with reference to the attached drawings.

DESCRIPTION OF THE EMBODIMENT

Next, an optical tomographic imaging apparatus according to an embodiment of the present invention is described.

Figure 1:
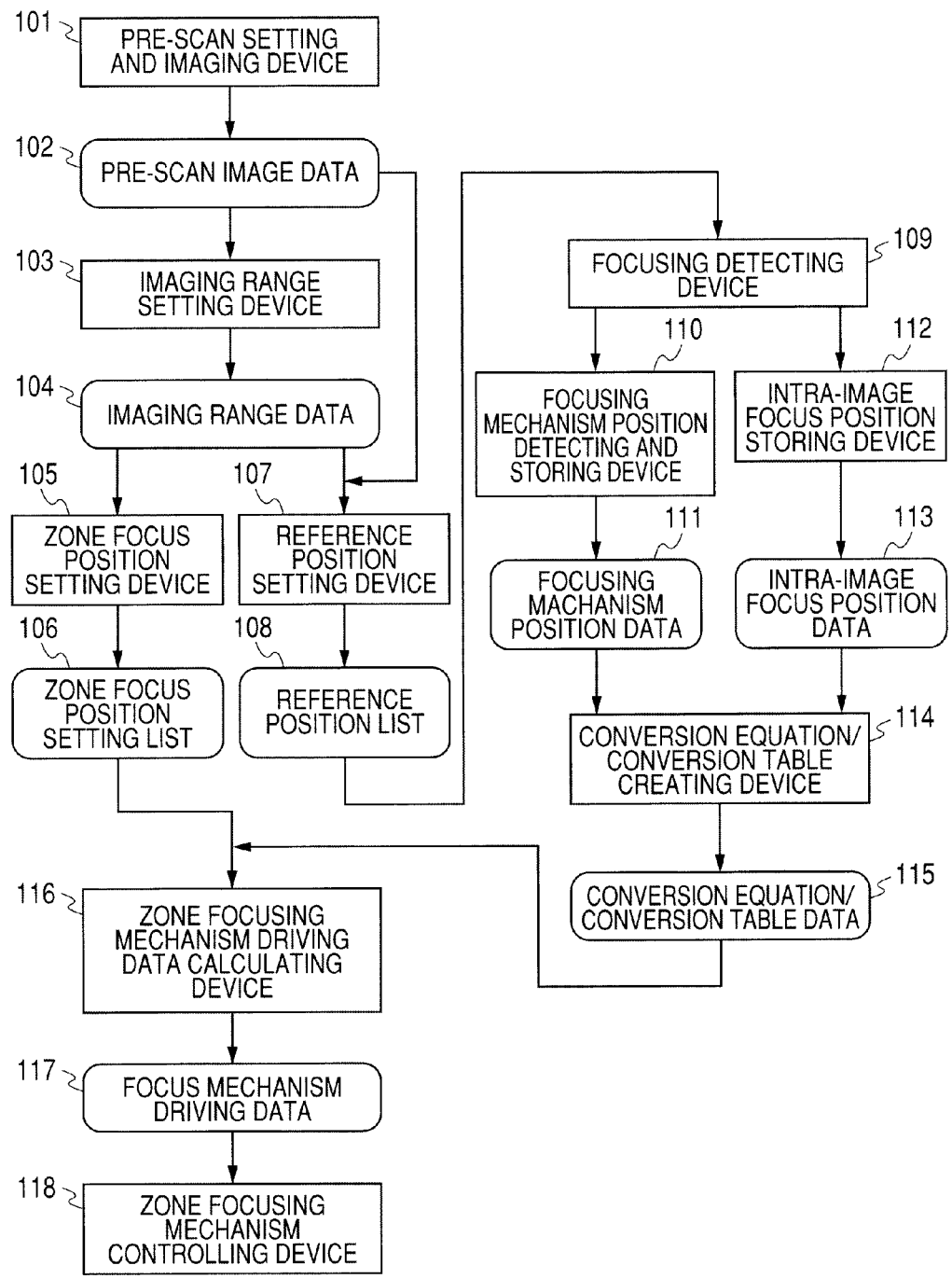
FIG. 1 is a schematic block diagram illustrating an overall function of a structural example of an optical tomographic imaging apparatus according to an embodiment of the present invention.

FIG. 1 is a schematic block diagram illustrating an overall function of a structural example of the optical tomographic imaging apparatus according to this embodiment.

In the optical tomographic imaging apparatus of this embodiment, a pre-scan setting and imaging device 101 performs pre-scan so that pre-scan image data 102 is obtained.

In the pre-scan, a reference beams delay position and a focus position are set roughly.

In other words, setting for obtaining an optimized image is not necessary as long as a profile image of an entire object can be obtained.

For instance, the pre-scan is performed after searching manually by an operator for a reference beams delay position and a focus position for obtaining a rough image.

Alternatively, one A-scan may be obtained automatically, before searching for a reference beams delay position having a signal.

On the other hand, luminance of the image (signal intensity) may be monitored roughly so as to adjust roughly the focus automatically so that a profile is shown.

Next, an imaging range setting device 103 sets a range in the depth direction for imaging based on the pre-scan image data 102, and hence imaging range data 104 is obtained.

Hereinafter, in the description of this embodiment, terms "range" and "position" are used for the depth direction. The range in the depth direction is simply referred to as a range, and the position in the depth direction is simply referred to as a position.

On the other hand, with regard to the horizontal direction, the range and the position thereof are referred to as a "horizontal direction range" and a "horizontal direction position" without abbreviation.

The range setting can be performed automatically for a range of the image luminance (OCT signal intensity) that is larger than or equal to a certain threshold value, or can be performed manually by an operator.

In a zone focus position setting device (focus position setting device) 105, a predetermined imaging depth range may be divided into multiple focus zones so that multiple focus positions are set.

In other words, multiple positions as zone focus positions are set by the zone focus position setting device 105 based on the imaging range data 104, and hence a zone focus position setting list 106 is created and stored.

On the other hand, a reference position setting device 107 sets at least two reference positions in the imaging depth direction within the predetermined imaging depth range.

The reference position setting device 107 obtains a reference position list 108 based on the imaging range data 104 and the pre-scan image data 102.

Specifically, approximately two to four parts having high image luminance (signal intensity) are selected from the pre-scan image so that the positions fall within the imaging range and are as distant from each other as possible. Those parts may be detected automatically or selected manually by an operator.

In particular, a retina of a human eye has high reflection layers at two regions positioned on substantial ends of a general imaging target range, which include:

(1) an optic nerve fiber layer on the surface (or inside); and
(2) a boundary between outer and inner of a photoreceptor cell or a pigmented epithelial cells layer.

Therefore, the reference position may be selected automatically by segmenting the reflection layers.

In addition, if the patient who has the individual variation or a disease is to be tested, the above-mentioned two regions are not always imaged and rendered as the high reflection layers. Therefore, the reference position may be selected by semiautomatic setting performed by an operator in the case of image structure different from a standard one.

The reference position list 108 is one-dimensional arrangement having elements of two reference positions (depth positions), for example, and the focus condition is obtained for each element by a focus detecting device 109.

Next, the focus detection performed by the focus detecting device of this embodiment is described.

Figure 2:
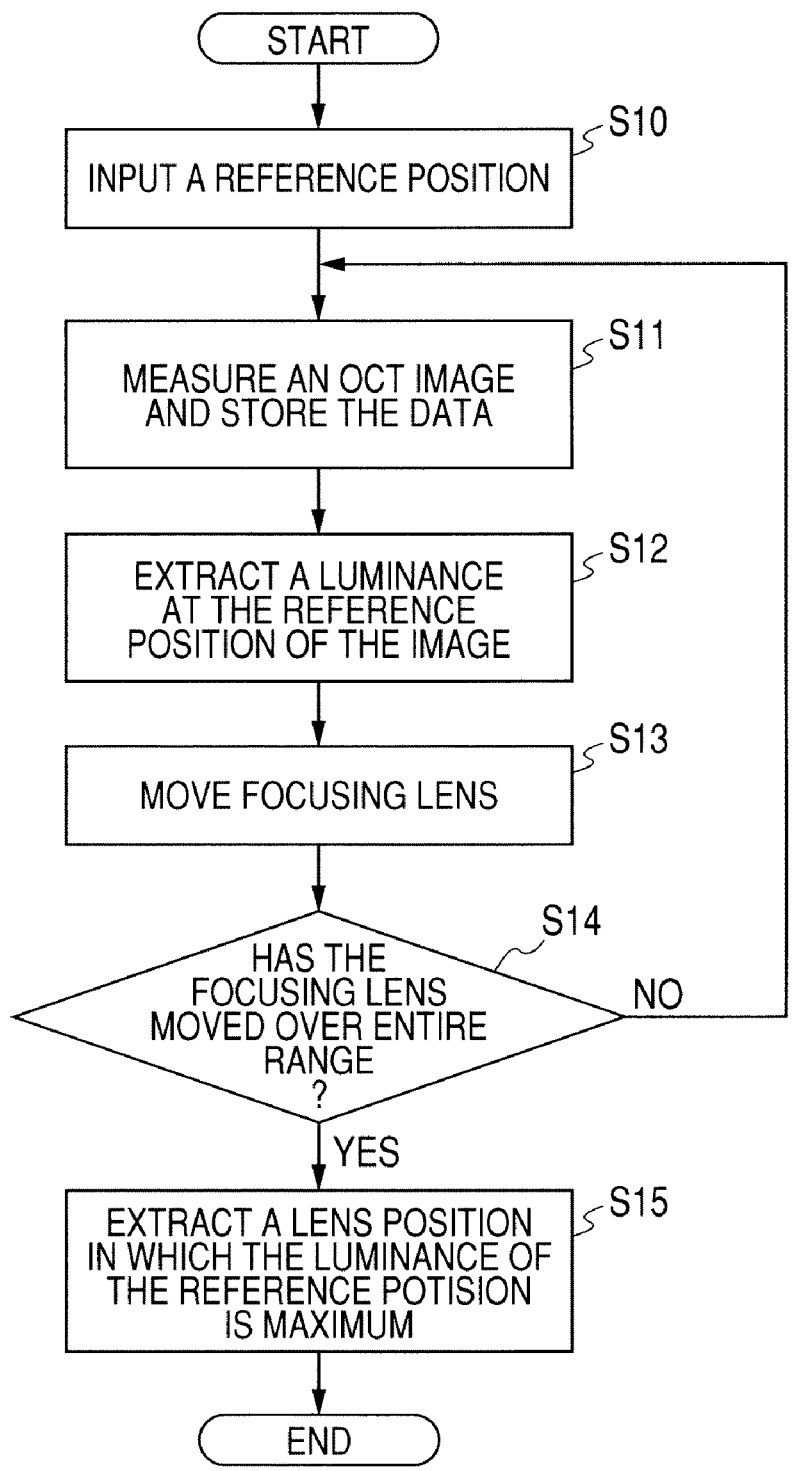
FIG. 2 is a flowchart illustrating focus detection by a focus detecting device in the optical tomographic imaging apparatus according to the embodiment of the present invention.

FIG. 2 is a flowchart of the focus detection performed by the focus detecting device of this embodiment.

First, input of the reference position (S10) is performed based on the above-mentioned reference position list 108, and then an OCT image is measured so as to store image data (S11).

Next, among the pieces of the stored image data, luminance at the reference position in the image is extracted, and the value thereof is stored (S12).

Next, the focusing lens is moved and is set to the next lens position (S13).

In this case, it is decided whether or not the focusing lens has moved over the entire range based on the above-mentioned imaging range data 104 (S14).

If the focusing lens has not moved over the entire range, the OCT image measuring and storing step (S11) and the subsequent steps are repeated.

If the focusing lens has moved over the entire range, the lens position, at which the image luminance at the reference position in the screen stored at each focus position is maximum, is determined by comparison (S15).

With the structure described above, one focus condition for the reference position in the image is determined first.

Note that the focus condition means correspondence between the position in the image and the position of the focusing lens.

A focusing mechanism position detecting and storing device 110 detects and holds focusing mechanism position data 111, while an intra-image focus position storing device 112 holds a corresponding intra-image focus position data 113.

Similarly, the focus condition is determined for each of the reference positions in the reference position list 108.

Next, a conversion equation/conversion table creating device (focus controlling data converting device) 114 generates and stores conversion equation/conversion table data 115 in which an intra-image focus position is an input and focusing mechanism position data is an output, based on multiple focus conditions.

Next, focus control is performed so that focusing is performed sequentially at the multiple focus positions, based on focus position information set by the focus position setting device and the focus conditions for focusing at two or more reference positions set in advance by the reference position setting device.

Specifically, a zone focusing mechanism driving data calculating device (focus driving information calculating device) 116 calculates driving information of the focus controlling device.

The calculation is performed by using the conversion equation or the conversion table created by the conversion equation/conversion table creating device 114 and the focus position information set by the focus position setting device.

In other words, the zone focus position setting list (focus position information) 106 and the conversion equation/conversion table data 115 are given to the zone focusing mechanism driving data calculating device 116 so that focusing mechanism driving data 117 is obtained.

According to the driving data, the zone focusing mechanism controlling device 118 controls to drive focusing mechanism elements sequentially so that focus to a desired in-screen focus position can be performed. Thus, if the OCT imaging is performed for every focus, a zone focusing type FD-OCT image with high horizontal resolution can be obtained efficiently.

The conversion equation is calculated by interpolation or extrapolation based on the multiple focus positions corresponding to actual OCT image data with respect to a human eye of an object having an individual variation.

Therefore, focus with high accuracy can be achieved and a number of focus positions can be determined efficiently. Because the zone focusing image can be obtained at high speed, a load on the patient as the object can be reduced.

Figure 3:
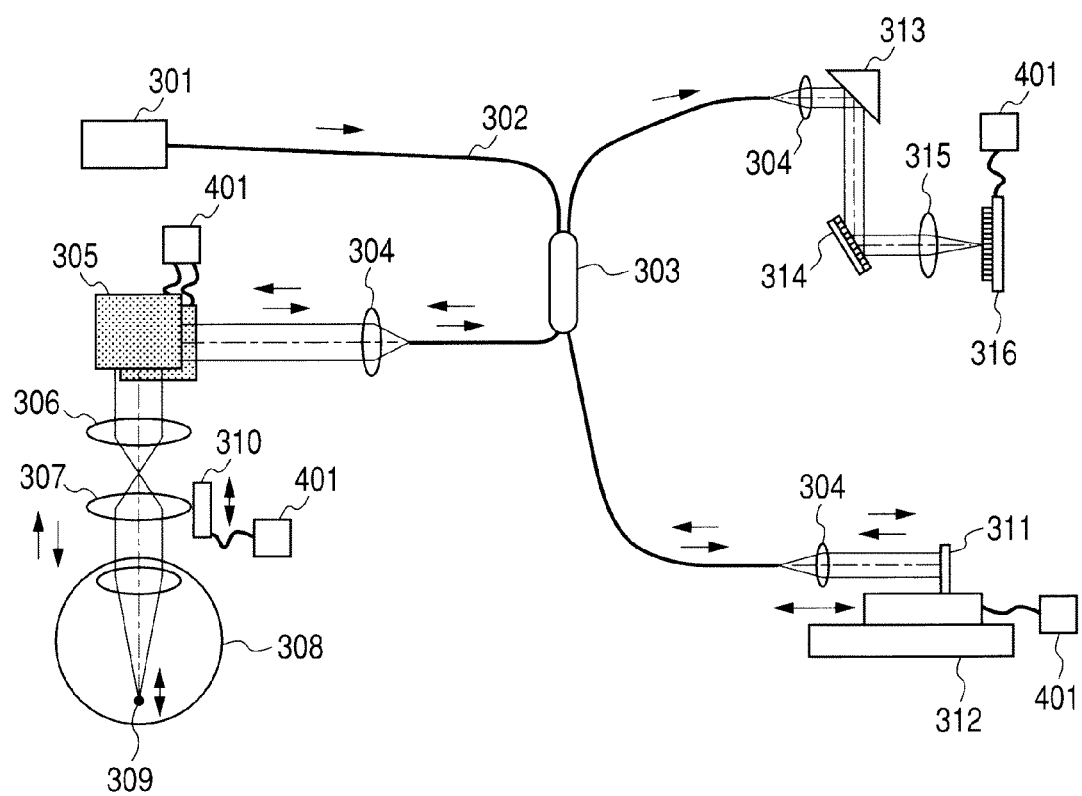
FIG. 3 is a diagram illustrating the structural example of the optical tomographic imaging apparatus according to the embodiment of the present invention.

Next, a structural example of the optical tomographic imaging apparatus according to this embodiment is described. FIG. 3 is a diagram illustrating the structural example of the optical tomographic imaging apparatus according to this embodiment.

Figure 4:
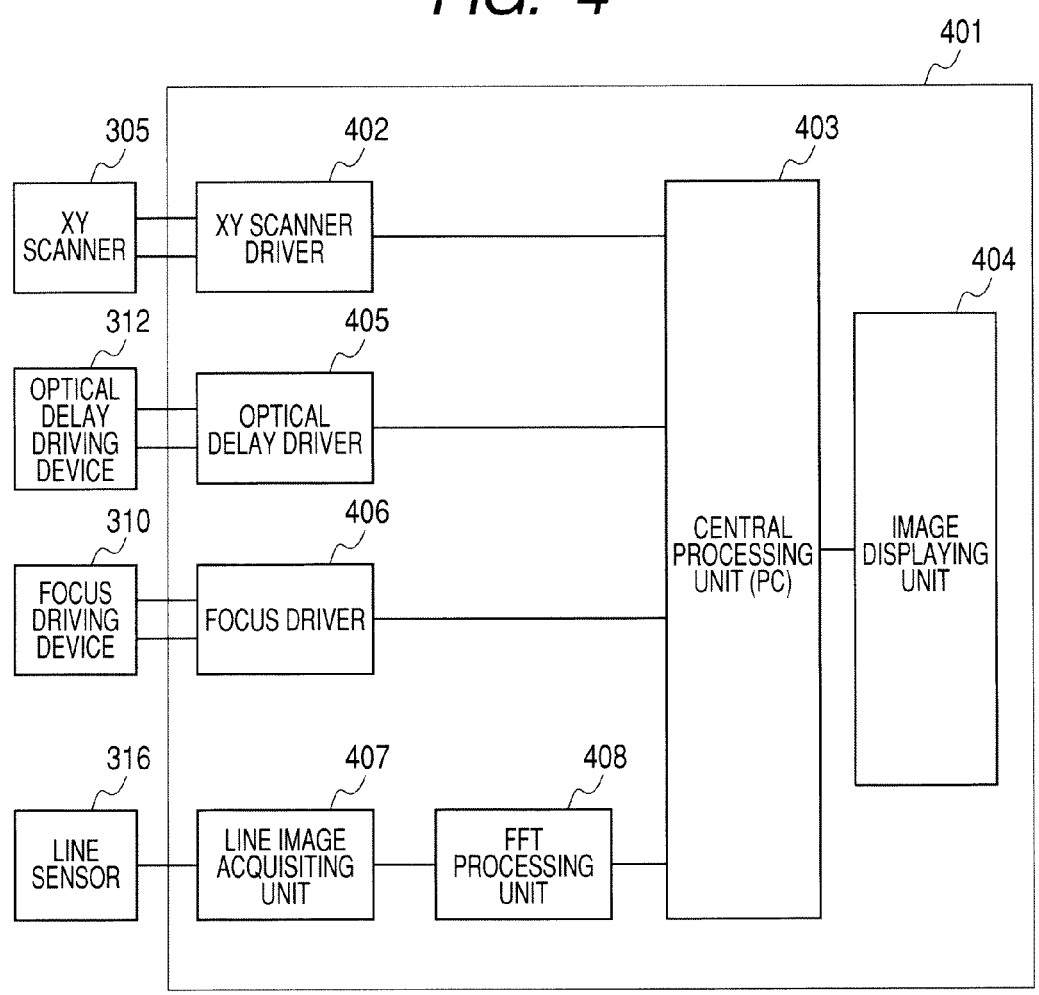
FIG. 4 is a schematic diagram illustrating an example of a controlling and signal processing device in the optical tomographic imaging apparatus according to the embodiment of the present invention.

FIG. 4 is a schematic diagram illustrating an example of a controlling and signal processing device 401 of the optical tomographic imaging apparatus of this embodiment.

In FIG. 3, a light source is represented by 301, an optical fiber is represented by 302, an optical fiber coupler is represented by 303, a collimate lens is represented by 304, an XY scanner is represented by 305, a scanning lens is represented by 306, an ocular lens is represented by 307, a human eye is represented by 308, and an optical interference imaging position is represented by 309.

Further, a focus driving actuator is represented by 310, a reference beams mirror is represented by 311, an optical delay driving apparatus is represented by 312, a reflecting mirror is represented by 313, a diffraction grating is represented by 314, an imaging lens is represented by 315, and a line sensor is represented by 316.

Figure 10A:
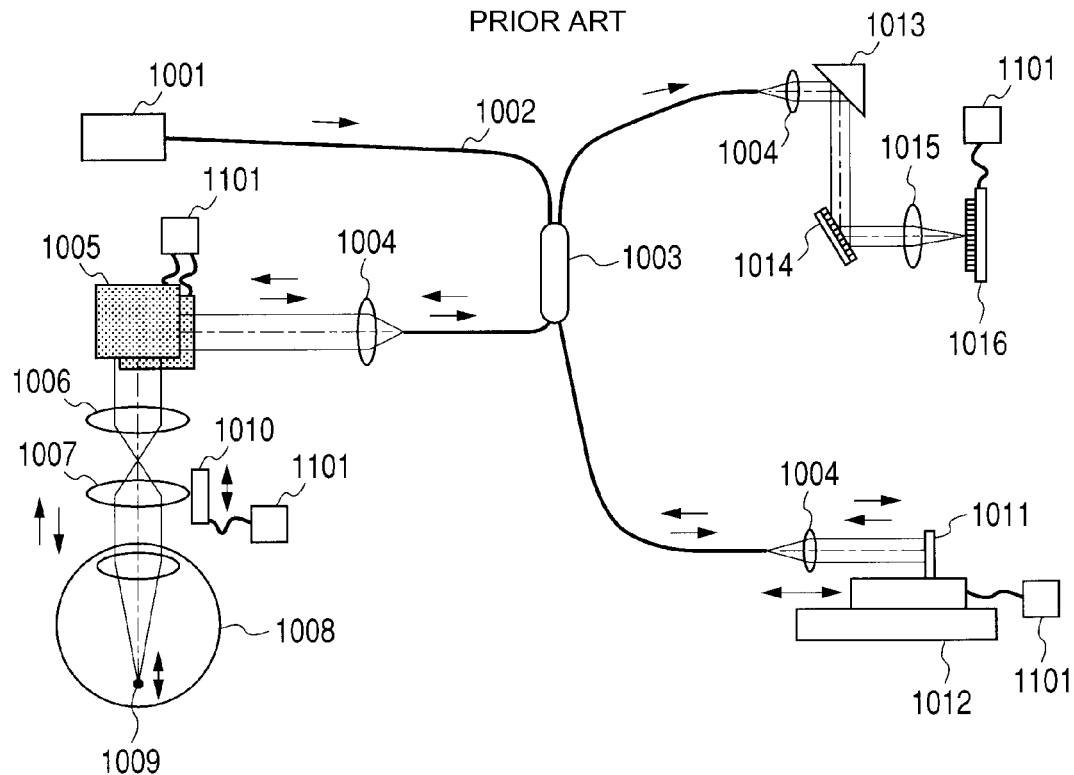
FIGS. 10A and 10B are schematic diagrams illustrating an FD-OCT in a conventional example.

The optical tomographic imaging apparatus of this embodiment has a structure that basically corresponds to that of the FD-OCT apparatus illustrated in FIG. 10A except for the controlling and signal processing device 401.

Figure 10B:
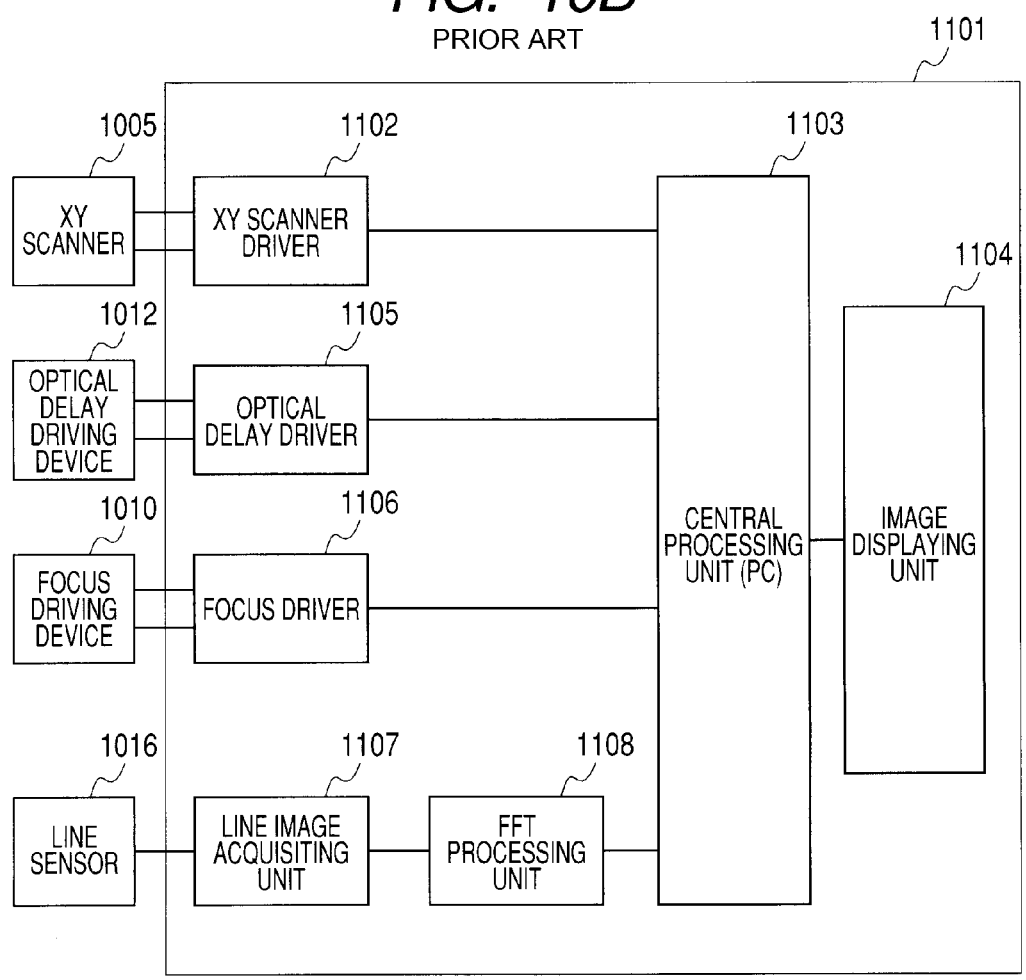

In addition, the controlling and signal processing device 401 controls the XY scanner 305, the optical delay driving apparatus 312, the focus driving actuator 310, and the line sensor 316, similarly to the structure illustrated in FIG. 10B. The controlling and signal processing device 401 also includes drivers and an acquisition unit for acquiring signals sent after detecting the angle, the position and an optical signal. Among the signals, a light intensity signal train transmitted from the line sensor is received by a line image acquisition unit 407, and inverse fast Fourier transform on the signal train is performed by an FFT processing unit 408. The result is sent to a central processing unit 403.

The central processing unit 403 receives the digital optical interference signal sent after the inverse Fourier transform in time series and compares the signal with each of the following signals.

The digital optical interference signal is compared with a scanner position signal and a synchronizing signal from an XY scanner driver 402, a delay position signal and a synchronizing signal from an optical delay driver 405, and a focus position signal from a focus driver 406.

Here, the light beams from the light source 301 is split into a measuring beams and a reference beams. The measuring beams is guided to the object through scanning with the scanning optical system (XY scanner 305 and scanning lens 306). The reference beams is guided to the reference beams mirror 311 and is reflected by the same. The measuring beams is reflected or scattered by the object (human eye 308) and becomes a return beams. The return beams and the reference beams reflected by the reference beams mirror are used for taking a tomographic image of the object.

In this case, in the optical tomographic imaging apparatus of this embodiment, the OCT apparatus is constituted, in which the optical tomographic image is imaged by the zone focusing in which the tomographic image is obtained as images split in the depth direction, which are recombined.

The structure described above is the same as that illustrated in FIGS. 10A and 10B except for the following points.

In the optical tomographic imaging apparatus of this embodiment, the focus driving actuator 310 illustrated in FIG. 3 drives the focus lens, and the corresponding focus driver 406 and central processing unit 403 illustrated in FIG. 4 perform the control as described above.

The central processing unit 403 controls the above-mentioned flow illustrated in FIG. 1. Upon necessity, the central processing unit 403 issue instructions to various drivers, receives a signal from the sensor, performs the imaging process appropriately, and displays the image on an image displaying unit 404.

Next, the individual steps of the flow in this embodiment illustrated in FIG. 1 are further described.

Figure 5A:
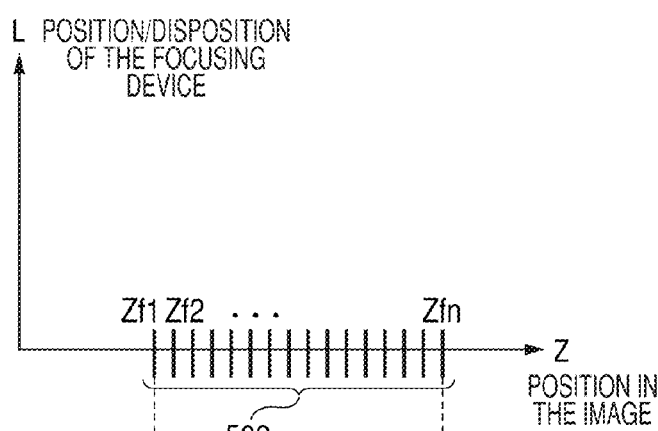
FIGS. 5A and 5B are schematic diagrams illustrating imaging range setting and zone focus position setting (FIG. 5A) as steps from a flow illustrated in FIG. 1 and a pre-scan image (FIG. 5B) in the embodiment of the present invention.
Figure 5B:
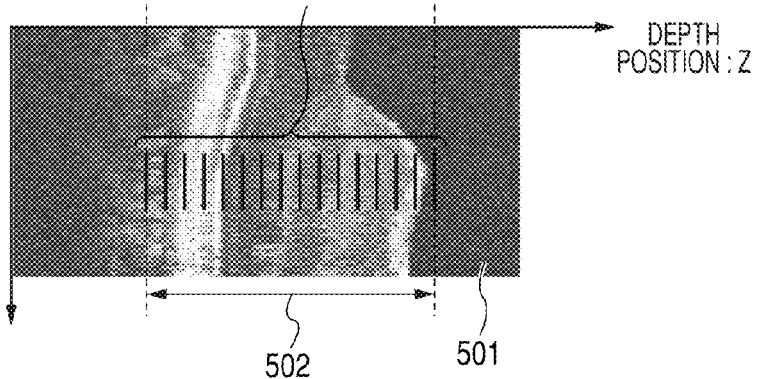

FIGS. 5A and 5B are schematic diagrams illustrating imaging range setting and zone focus position setting as steps of the flow illustrated in FIG. 1, as well as a pre-scan image in this embodiment.

FIG. 5B illustrates how an imaging range 502 is set based on a pre-scan image 501. FIG. 5A illustrates how zone focus positions 503 are set by evenly splitting the range at predetermined intervals.

Note that a position in the image (Z axis) of FIG. 5A as well as FIGS. 7A, 8A, and 9A that are referred to later corresponds to a delay adjusting mirror position in the reference beams path in the interferometer.

Figure 6A:
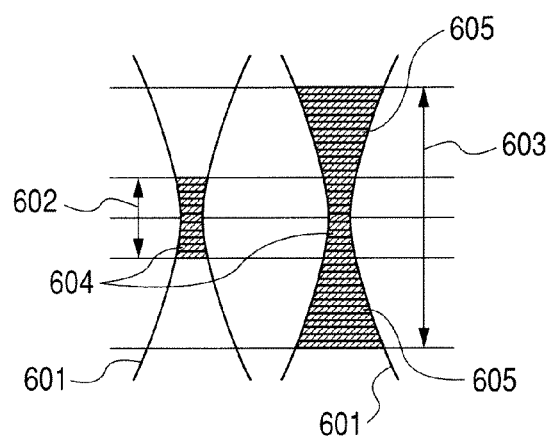
FIGS. 6A, 6B and 6C are schematic diagrams illustrating an example of two different modes by the zone focus position setting as the step from the flow illustrated in FIG. 1 in the embodiment of the present invention.
Figure 6B:
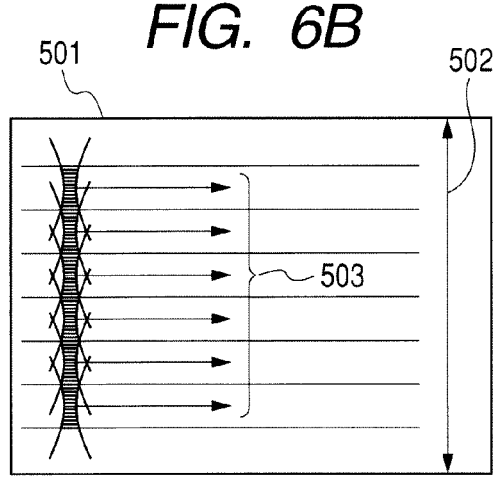
Figure 6C:
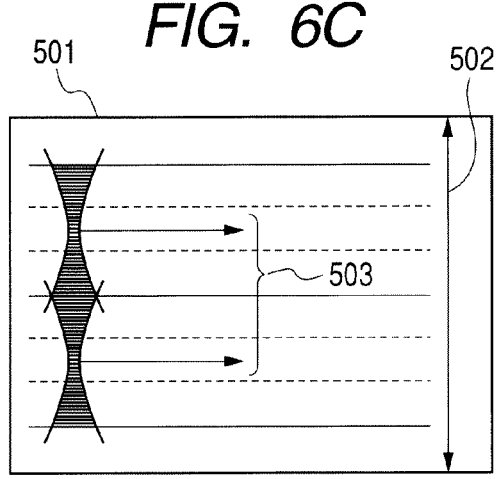

FIGS. 6A, 6B and 6C are schematic diagrams illustrating examples of two different modes by the zone focus position setting as the step of the flow illustrated in FIG. 1 in this embodiment.

The left part of FIG. 6A and FIG. 6B illustrate the case where an OCT pixel 604 is obtained by setting the range of a depth of focus 602 in which the beams diameter is 1.4 times a beams waist with respect to a condensed beams 601 (range in which a so-called confocal parameter b is positioned on both sides of the beams waist), as a range of one zone.

This is the case where a horizontal resolution emphasized mode is set.

The right side of FIG. 6A and FIG. 6C illustrate the case where an OCT pixel 605 is obtained by setting a range 603 in which the beams diameter is square root of 10 times of the beams waist with respect to the same condensed beams 601 and beams irradiation intensity per unit area becomes approximately one tenth, as the range of one zone. This is the case where a luminance emphasized mode is set with a criterion of 10-dB drop of the image luminance.

The latter mode puts weight on solving the problem that, if the depth of focus is small, not only the horizontal resolution is deteriorated on both sides of the imaging range but also the image luminance is decreased so that the image itself may disappear, because the OCT utilizes the confocal optical structure.

As described above, the optical tomographic imaging apparatus of this embodiment may include a mode selecting device for selecting at least one mode from multiple modes including a horizontal resolution mode and a luminance mode.

Thus, the imaging range can be set appropriately. Then, the focus position setting device sets the focus position based on the selected mode.

Figure 7A:
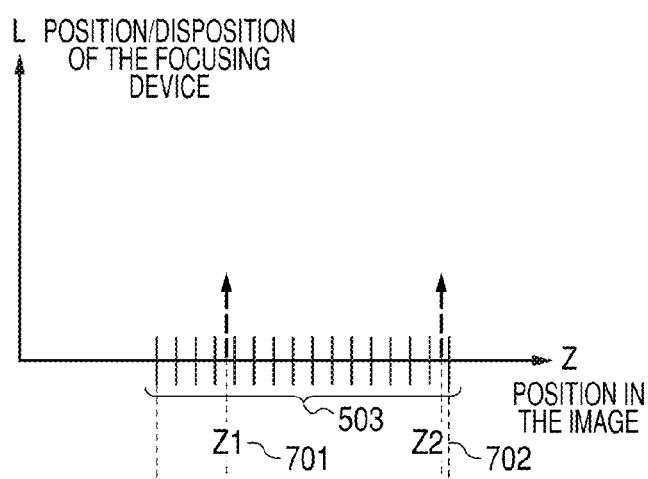
FIGS. 7A and 7B are schematic diagrams illustrating the imaging range setting and reference position setting (FIG. 7A) as steps from the flow illustrated in FIG. 1 and a pre-scan image (FIG. 7B) in the embodiment of the present invention.
Figure 7B:
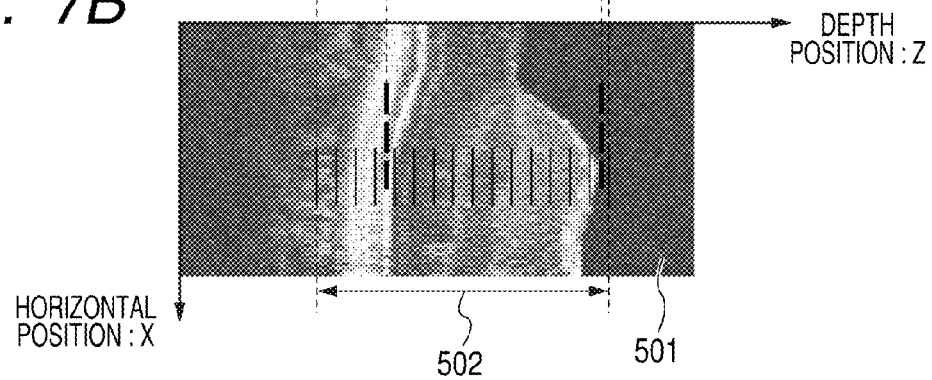

FIGS. 7A and 7B are schematic diagrams illustrating the imaging range setting and reference position setting as steps of the flow illustrated in FIG. 1 and a pre-scan image in this embodiment.

Based on the pre-scan image 501 and the imaging range 502 illustrated in FIG. 7B, a first reference position 701 (Z1) and a second reference position 702 (Z2) are set as two positions having high luminance in the image and being as distant as possible from each other in the imaging range as illustrated in FIG. 7A.

Figure 8A:
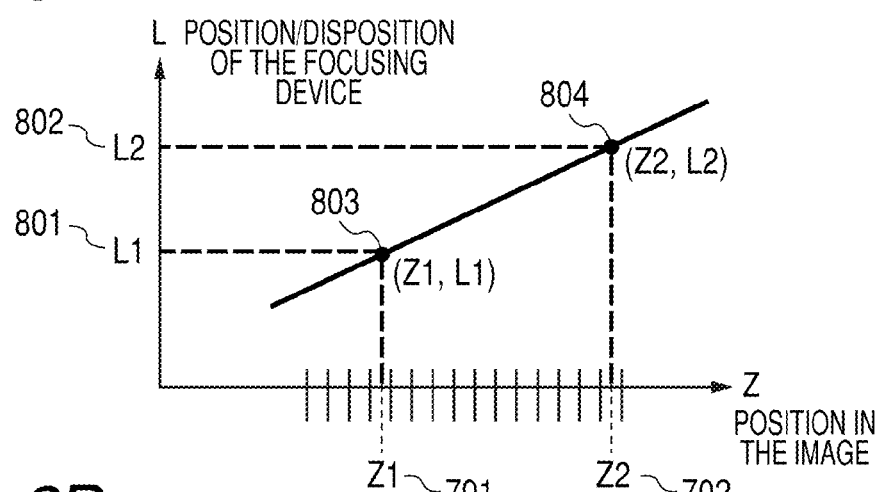
FIGS. 8A and 8B are schematic diagrams illustrating how multiple focus conditions and a conversion equation are obtained, as a step from the flow illustrated in FIG. 1 in the embodiment of the present invention.
Figure 8B:
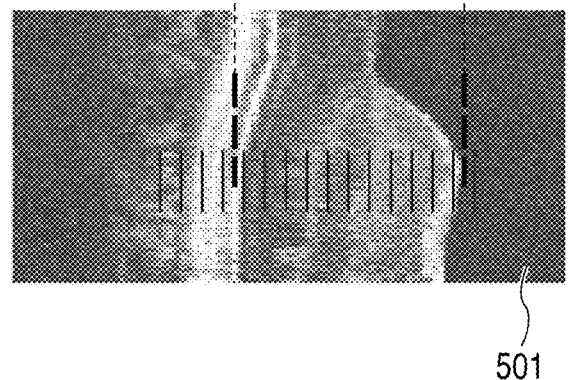

FIGS. 8A and 8B are schematic diagrams illustrating how multiple focus conditions and a conversion equation are obtained, as a step of the flow illustrated in FIG. 1 in this embodiment.

FIGS. 8A and 8B illustrate the manner as follows.

With respect to the first reference position 701 and the second reference position 702 illustrated in FIG. 8B, focus detection is performed, so as to detect and store the corresponding focusing lens positions (first focusing position 801 (L1) and second focusing position 802 (L2)) as illustrated in FIG. 8A.

As a result, two focus conditions 803 and 804 are obtained as the two-dimensional arrangement. Then, a linear function 805 is obtained as the conversion equation.

Figure 9A:
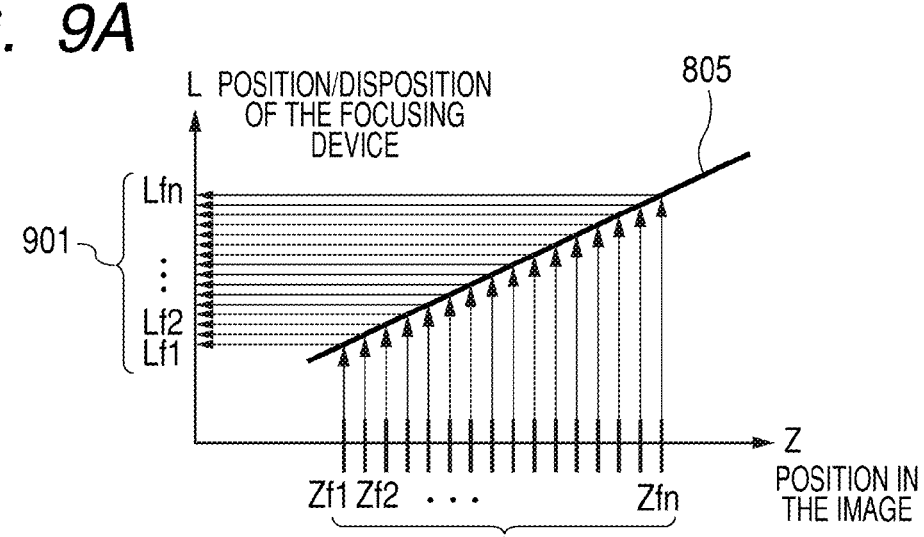
FIGS. 9A and 9B are schematic diagrams illustrating how multiple positions of a focusing device are obtained from the conversion equation, as a step from the flow illustrated in FIG. 1 in the embodiment of the present invention.
Figure 9B:
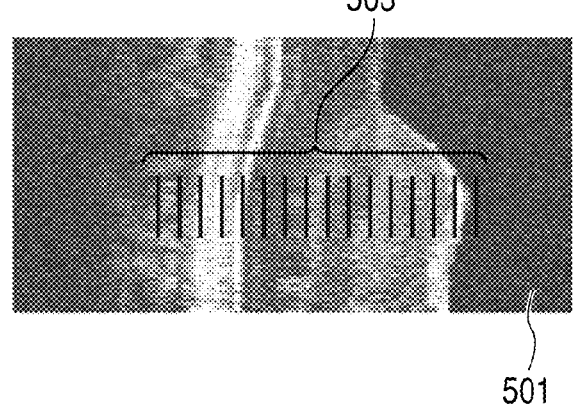

FIGS. 9A and 9B are schematic diagrams illustrating how multiple positions of a focusing device are obtained from the conversion equation, as a step of the flow illustrated in FIG. 1 in this embodiment. FIGS. 9A and 9B illustrate how $Zf1$, $Zf2, \ldots, Zfn$ as elements of the zone focus positions 503 are converted by the linear function 805 as the conversion equation so that elements $Lf1, Lf2, \ldots, Lfn$ of focusing positions 901 are obtained.

With the structure of this embodiment described above, the OCT imaging of a human eye having an individual variation can be performed with high accuracy, high efficiency and high horizontal resolution. Thus, a high performance optical tomographic imaging apparatus (optical interference tomographic imaging apparatus) that can reduce a load on a patient as an object may be realized.

However, the present invention is not limited to the structure of the embodiment described above.

For instance, the focusing mechanism in the embodiment described above moves the focusing lens, but focusing with the mirror system may be adopted. In this case, a deformation of the mirror can be utilized.

In addition, for example, in the embodiment described above, in the focus detection, the in-focus state is decided by detecting the maximum luminance at the reference position in the image, but needless to say, the in-focus state is decided based on definition of the image, for example.

In this case, for example, a contrast with respect to a space frequency may be calculated like a modulation transfer function (MTF) so that the in-focus state is decided.

Further, a characteristic matter in the image may be set so that the in-focus state is decided based on definition of a contour or the like of the characteristic matter.

In addition, for example, the embodiment described above exemplifies two reference positions, and needless to say, the conversion equation may be a linear function indicating a straight line passing through the two points in this case.

If the number of the reference positions is three or larger, one of methods may be selected appropriately, such as a method of performing straight line (linear function) fitting by the least-square method, a method of using a second or higher order function, and a method of performing spline interpolation. Further, the conversion equation may be a discrete table instead of a continuous function.

Therefore, the present invention is not limited to the number of the reference positions or a type of the conversion equation or the conversion table.

However, if the number of the reference positions is too large, contradiction would occur to the point of the present invention that is to perform focusing in many positions efficiently with a small number of actual focus detections. Therefore, it is not practical to set, for example, ten or more reference positions.

The high resolution OCT optical interferometer apparatus of the present invention is suitable for imaging a retina of a human eye, in particular. However, the high resolution OCT optical interferometer apparatus can also be used as various diagnosis apparatuses or inspection apparatuses for observation of a living organism such as a skin or an organ using an endoscope, or an industrial quality control.

OTHER EMBODIMENTS

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-011619, filed Jan. 22, 2009, which is hereby incorporated by reference herein in its entirety.

What is claimed is:

1. An optical tomographic imaging apparatus that takes a tomographic image of an object by splitting light from a light source into a measuring light and a reference light, guiding the measuring light to the object through scanning with a scanning optical system, and using a return light, which corresponds to the measuring light that is reflected or scattered by the object, and the reference light, the optical tomographic imaging apparatus comprising:
   a pre-scan imaging unit configured to take a tomographic pre-scan image;
   a focus position setting unit configured to set multiple focus positions within a predetermined imaging depth range of the pre-scan image;
   a reference position setting unit configured to set at least two reference positions in an imaging depth direction within the predetermined imaging depth range;
   a focus detecting unit configured to detect a focus condition of in-focus at the at least two reference positions; and
   a focus controlling unit configured to control the performance of focusing at the multiple focus positions sequentially based on the focus condition of in-focus.

2. The optical tomographic imaging apparatus according to claim 1, further comprising:
   a focus controlling data converting unit configured to create one of a conversion equation and a conversion table, in which a focus position in the imaging depth direction within the tomographic image is an input and position information of a focusing mechanism is an output, based on the focus condition of the in-focus detected by the focus detecting unit, and storing the one of the conversion equation and the conversion table so as to convert the input into the output; and
   a focus driving information calculating unit configured to calculate driving information of the focusing mechanism based on the one of the conversion equation and the conversion table created by said focus controlling data converting unit and on the focus position information from said focus position setting unit,
   wherein the focusing mechanism is driven and controlled by the focus controlling unit according to the driving information.

3. The optical tomographic imaging apparatus according to claim 1, wherein the focus detecting unit detects the focus condition of in-focus by determining an in-focus state for the at least two reference positions based on luminance of a the pre-scan image of the predetermined imaging depth range.

4. The optical tomographic imaging apparatus according to claim 1, wherein the focus detecting unit detects the focus condition of in-focus by determining an in-focus state for the at least two reference positions based on a definition of the pre-scan image of the predetermined imaging depth range.

5. The optical tomographic imaging apparatus according to claim 1, further comprising:
   a mode selecting unit configured to select at least one mode from among multiple modes including a horizontal resolution mode and a luminance mode,
   wherein the luminance mode uses a pixel larger than that of the horizontal resolution mode, and
   wherein said focus position setting unit sets the multiple focus positions based on the at least one mode that has been selected.

6. An imaging method of taking a tomographic image of an object by splitting a light from a light source into a measuring light and a reference light, guiding the measuring light to the object through scanning with a scanning optical system, and using a return light corresponding to the measuring light that is reflected or scattered by the object and the reference light, the imaging method comprising:

a pre-scan imaging step of taking a tomographic pre-scan image;

a first setting step of setting multiple focus positions within a predetermined imaging depth range of the pre-scan image;

a second setting step of setting at least two reference positions in an imaging depth direction within the predetermined imaging depth range;

a focus detecting step of detecting a focus condition of in-focus at the at least two reference positions; and a focusing step of focusing at the multiple focus positions sequentially based on the focus condition of in-focus.

7. A non-transitory computer-readable storage medium storing a program that causes a computer to execute the imaging method according to claim 6.

* * * * *